(12) United States Patent
Benage et al.

(10) Patent No.: US 6,653,414 B2
(45) Date of Patent: Nov. 25, 2003

(54) INHIBITION OF POLYMERIZATION OF UNSATURATED MONOMERS

(75) Inventors: Brigitte Benage, Wolcott, CT (US); Brendan J. Geelan, East Haven, CT (US); Gerald J. Abruscato, Southington, CT (US); Leo Bonnell, Hellertown, PA (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 135 days.

(21) Appl. No.: 09/916,580

(22) Filed: Jul. 30, 2001

(65) Prior Publication Data

US 2002/0037958 A1 Mar. 28, 2002

Related U.S. Application Data

(63) Continuation-in-part of application No. 09/452,972, filed on Dec. 2, 1999.

(51) Int. Cl.⁷ .............................. C08F 2/38; C07C 7/20; C07D 211/40
(52) U.S. Cl. ............................ 526/83; 585/5; 546/216; 546/223; 560/205; 564/297
(58) Field of Search .......................... 526/83; 560/205; 546/216, 223; 545/297; 585/5

(56) References Cited

U.S. PATENT DOCUMENTS

| | | | |
|---|---|---|---|
| 3,163,677 A | 12/1964 | Hoffman et al. | 260/583 |
| 3,253,055 A | 5/1966 | Goble et al. | 260/638.75 |
| 3,334,103 A | 8/1967 | Feldman et al. | 260/290 |
| 3,372,182 A | 3/1968 | Hoffmann et al. | 260/465.5 |
| 3,422,144 A | 1/1969 | Hoffmann et al. | 260/570 |
| 3,494,930 A | 2/1970 | Dupeyre et al. | 260/294.7 |
| 3,502,692 A | 3/1970 | Feldman et al. | 260/326.3 |
| 3,704,233 A | 11/1972 | Eich et al. | 260/285.5 |
| 3,873,564 A | 3/1975 | Schneider et al. | 260/309.6 |
| 3,966,711 A | 6/1976 | Rasberger | 260/239.3 |
| 4,182,658 A | 1/1980 | Watson | 203/9 |
| 4,665,185 A | 5/1987 | Winter et al. | 546/184 |
| 5,254,760 A | 10/1993 | Winter et al. | 585/435 |
| 5,290,888 A | 3/1994 | Gatechair et al. | 526/83 |
| 5,545,782 A | 8/1996 | Winter et al. | 585/435 |
| 5,545,786 A | 8/1996 | Winter et al. | 585/435 |
| 5,877,344 A | 3/1999 | Gande et al. | 560/205 |

FOREIGN PATENT DOCUMENTS

| | | |
|---|---|---|
| CZ | 260755 B1 | 1/1989 |
| EP | 0 178 168 A2 | 10/1985 |
| EP | 0737660 A1 | 10/1996 |
| EP | 0 765 856 A1 | 4/1997 |
| EP | 1065197 A1 | 1/2001 |
| FR | 2761060 | 8/1999 |
| GB | 1127127 | 4/1966 |
| SU | 478838 | 7/1975 |
| SU | 334845 A1 | 1/1984 |
| WO | 97/46504 | 12/1997 |
| WO | 98/02403 | 1/1998 |
| WO | WO 98/14416 | 4/1998 |
| WO | 98/25872 | 6/1998 |
| WO | WO 98/45385 | 10/1998 |
| WO | 00/14039 | 3/2000 |

OTHER PUBLICATIONS

Lartigue–Peyrou et al. "Composition and its use for inhibiting radical . . . " CA 129:302959 (1998).*
Zhang et al."Inhibiting reactions of radical polyerization of vinyl monomers V . . . " CA 100:175349 (1984).*
Zhang et al."Inhibiting effect of radical polymerization of vinyl monomers VI . . . " CA 106:120263 (1986).*
Wang et al., Lanzhou Daxue Xuebao, Ziran Kexueban 23(3):138–140 (1987).
Ind. Chem. Libr., The Use of Phenolic Compounds as Free–Radical Polymerization Inhibitors, (1996), pp. 489–505.

* cited by examiner

*Primary Examiner*—Ceila Chang
(74) *Attorney, Agent, or Firm*—Michael P. Dilworth; Paul Grandinetti (57) ABSTRACT

Disclosed herein is a method for inhibiting the premature polymerization of ethylenically unsaturated monomers comprising adding to said monomers an effective amount of a mixture comprising:

A) at least one stable hindered nitroxyl compound having the structural formula:

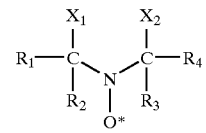

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, $-S-COR_7$, $-OCOR_7$, (wherein $R_7$ is alkyl or aryl), amido, $-S-C_6H_5$, carbonyl, alkenyl, or alkyl of 1 to 15 carbon atoms, or (2) taken together, form a ring structure with the nitrogen; and B) at least one inhibitor selected from the group consisting of ortho-quinone, ortho-hydroquinone, para-quinone, para-hydroquinone, and derivatives of the foregoing.

58 Claims, 2 Drawing Sheets

FIG. 1

INHIBITION OF POLYMERIZATION OF UNSATURATED MONOMERS

CROSS REFERENCE TO RELATED APPLICATION

This application is a continuation-in-part of co-pending application Ser. No. 09/452,972 filed Dec. 2, 1999.

BACKGROUND OF THE INVENTION

1. Field of the Invention

The present invention is directed to the use of a combination of at least one stable nitroxide free radical compound and at least one quinone and/or hydroquinone (hereinafter, quinone/hydroquinone) to inhibit the polymerization of ethylenically unsaturated monomers.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of the monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

A wide variety of compounds has been proposed and used for inhibiting uncontrolled and undesired polymerization of ethylenically unsaturated monomers. However, these compounds have not been fully satisfactory. In particular, there is a need for an inhibitor that not only provides highly effective inhibition of polymerization during normal operation of a continuous manufacture or purification process, but also provides satisfactory protection in the event of a loss of continuous inhibitor feed. While many inhibitors are known to provide sufficient protection in one of these scenarios, these inhibitors have not been fully satisfactory under both normal and upset operating conditions. Accordingly, there has been a substantial need in the art for improved compositions for inhibiting the polymerization of such monomers during their production and the distillation process for purifying or separating them from impurities, as well as during transport and storage.

Hindered nitroxyl compounds are known to be very active inhibitors of free radical polymerizations of unsaturated monomers such as styrene, acrylic acid, methacrylic acid, and the like. Quinones and hydroquinones are also known to have a similar capacity.

U.S. Pat. No. 3,163,677 discloses N,N,O-trisubstituted hydroxylamines and N,N-disubstituted nitroxides of the formulae:

wherein $R_1$, $R_2$, and $R_3$ are each an alkyl radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,334,103 discloses that nitroxides can be prepared from the corresponding heterocyclic amine wherein the nitrogen atom of the nitroxide group is attached to other than a tertiary carbon of an aliphatic group (i.e., the nitrogen atom forms a part of a heterocyclic nucleus). These nitroxides are said to have useful properties similar to those described for the N,N-disubstituted nitroxides of U.S. Pat. No. 3,163,677.

U.S. Pat. No. 3,372,182 discloses that a great variety of N,N-disubstituted, stable, free radical nitroxides not otherwise readily available can be prepared by a simple and convenient process that comprises pyrolyzing in an inert reaction medium virtually any hydroxylamine that is susceptible to cleavage of the O—C bond, e.g., tri-t-butylhydroxylamine.

U.K. Patent Number 1,127,127 discloses that acrylic acid can be stabilized against polymerization by the addition thereto of a nitroxide having the essential skeletal structure:

wherein $R_1$, $R_2$, $R_3$, and $R_4$ are alkyl groups and no hydrogen is bound to the remaining valencies on the carbon atoms bound to the nitrogen. The two remaining valencies that are not satisfied by $R_1$ to $R_4$ or nitrogen can also form part of a ring (e.g., 2,2,6,6 tetramethyl-4-hydroxy-piperidine-1-oxyl).

U.S. Pat. No. 3,422,144 discloses stable, free radical nitroxides of the formula:

wherein R is selected from the group consisting of tertiary alkyl, aryl, alkaryl, haloaryl, carboxyaryl, alkoxyaryl, alkylthioaryl, pyridyl, and dialkylaminoaryl, and R' is tertiary alkyl. These nitroxides are said to be useful as traps for reactive free radicals both in the counting of free radicals and for inhibiting oxidation and free radical polymerization.

U.S. Pat. No. 3,494,930 discloses free radicals of the nitroxide type for use as initiators of free radical reactions, collectors of free radicals, polymerization inhibitors or antioxidants. They are constituted by nitrogenous bicyclic compounds in which one of the bridges comprises solely the nitroxide radical group and, in particular, by aza-9-bicyclo (3,3,1) nonanone-3-oxyl-9, and by aza-9-bicyclo (3,3,1) nonane oxyl-9.

U.S. Pat. No. 3,873,564 discloses compounds and a method for assaying enzymes by adding to a medium containing an enzyme a stable free radical compound having a stable free radical functionality which, when subjected to an enzyme-catalyzed reaction, changes the environment of the free radical functionality. By following the change in the electron spin resonance spectrum as affected by the change in environment, the type of enzyme and the activity of the enzyme can be determined.

The compounds found useful are normally stable nitroxide radicals with an enzyme labile functionality. Other compounds include two cyclic nitroxide containing rings joined by a chain having an enzyme labile functionality.

U.S. Pat. No. 3,966,711 teaches that 2,2,7,7-tetraalkyl- and 2,7-dispiroalkylene-5-oxo-1,4-diazacycloheptanes substituted in the 4-position by mono- or tetravalent radicals are powerful light-stabilizers for organic polymers. They are said to possess higher compatibility than their 4-unsubstituted homologues, from which they can be synthesized by reactions known for N-alkylation. Preferred substituents in the 4-position are alkyl, alkylene, alkenyl, aralkyl, and esteralkyl groups. The 1-nitroxyls derived from the imidazolidines by oxidation with hydrogen peroxide or percarboxylic acids are also said to be good light stabilizers.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

European Patent Application 0 178 168 A2 discloses a method for inhibiting the polymerization of an $\alpha,\beta$-ethylenically unsaturated monocarboxylic acid during its recovery by distillation by using a nitroxide free radical.

U.S. Pat. No. 4,665,185 discloses a process for the efficient preparation of nitroxyls of sterically hindered amines by the oxidation of the amine using a hydroperoxide in the presence of a small amount of a metal ion catalyst, at moderate temperature for a short period of time, to give the nitroxyl in high yield and purity.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c). According to the specification, examples of suitable nitroxide free radical compounds include di-t-butylnitroxide; di-t-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-dimethylamino-2,2,6,6-tetramethyl-piperidinyloxy; 4-amino-2,2,6,6-tetramethyl-piperidinyloxy; 4-ethanoyloxy-2,2,6,6-tetramethyl-piperidinyloxy; 2,2,5,5-tetramethylpyrrolidinyloxy; 3-amino-2,2,5,5-tetramethylpyrrolidinyloxy; 2,2,5,5-s tetramethyl-1-oxa-3-azacyclopentyl-3-oxy; 2,2,5,5-tetramethyl-1-oxa-3-pyrrolinyl-1-oxy-3-carboxylic acid; and 2,2,3,3,5,5,6,6-octamethyl-1,4-diazacyclohexyl-1,4-dioxy.

WO 97/46504 concerns substance mixtures containing: (A) monomers containing vinyl groups; and (B) an active amount of a mixture which inhibits premature polymerization of the monomers containing vinyl groups during their purification or distillation and contains: (i) between 0.05 and 4.5 wt %, relative to the total mixture (B), of at least one N-oxyl compound of a secondary amine which has no hydrogen atom at the $\alpha$-C atoms; and (ii) between 99.95 and 95.5 wt % relative to the total mixture (B), of at least one nitro compound. The publication also discloses a process for inhibiting the premature polymerization of monomers, and the use of mixture (B) for inhibiting the premature polymerizatin of monomers.

WO 98/02403 relates to inhibiting the polymerization of vinyl aromatic compounds by using a mixture of a phenol and a hydroxylamine. It is said that the process is useful in ethylbenzene dehydrogenation effluent condenser systems and styrene-water separator vent gas compressor systems and that it effectively inhibits polymerization of monomers, preventing the formation of a polymer coating on condenser and compressor equipment, thus reducing the necessity for cleaning of equipment surfaces.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing: (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the $\alpha$-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

CS-260755 B1 is directed to the preparation of 4-substituted-2,2,6,6-tetramethylpiperidine nitroxyls as olefin stabilizers.

SU-334845 A1 is directed to the inhibition of the radical polymerization of oligoester acrylates using iminoxyl radical inhibitors of a given formula.

SU-478838 is directed to the inhibition of the radical polymerization of oligoester acrylates and the prevention of oligomeric peroxides using a binary polymerization inhibitor comprising quinone.

FR 2,761,060 relates to the prevention of premature polymerization of styrene during its production by dehydrogenation of ethylbenzene by injecting into the process effluent a radical inhibitor based on an oxyl-tetramethylpiperidine derivative.

Wang et al., *Lanzhou Daxue Xuebao, Ziran Kexueban* 23(3):138–140 (1987) evaluated the inhibition effect of the stable nitroxide free radical, di-t-butylnitroxide, on the polymerization of acrylic acid and styrene monomers by three methods: separation method, reboiling method, and expanding method. The results showed that di-t-butylnitroxide itself has an inhibiting effect, and when it blends with hydroquinone, t-butyl catechol, benzoquinone, the inhibition effect is better than common inhibitors.

The foregoing are incorporated herein by reference in their entirety.

SUMMARY OF THE INVENTION

As used herein, the abbreviation TEMPO stands for 2,2,6,6-tetramethyl-1-piperidinyloxy. Thus, 4-amino-TEMPO is 4-amino-2,2,6,6-tetramethyl-1-piperidinyloxy; 4-hydroxy-TEMPO is 4-hydroxy-2,2,6,6-tetramethyl-1-piperidinyloxy (also known in the art as HTEMPO); 4-oxo-TEMPO is 4-oxo-2,2,6,6-tetramethyl-1-piperidinyloxy; and so on.

As mentioned above, (a) hindered nitroxyl compounds and (b) quinones and/or hydroquinones are each separately known to be very active inhibitors of free radical polymerizations of unsaturated monomers. The present invention is directed to the discovery that a mixture of at least one stable hindered nitroxyl compound (e.g., 4-amino-TEMPO or 4-oxo-TEMPO) with at least one quinone/hydroquinone provides better performance than either component alone, as indicated by both the low polymer numbers at steady state and the slow rate of polymerization after shutoff of feed in a steady state dynamic testing system.

More particularly, the present invention is directed to a method for inhibiting the premature polymerization of ethylenically unsaturated monomers comprising adding to said monomers an effective amount of a mixture comprising:

A) at least one inhibitor having the following structural formula:

(I)

and

B) at least one inhibitor selected from the group consisting of ortho-quinone, ortho-hydroquinone, para-quinone, para-hydroquinone, and derivatives of the foregoing.

In formula (I), $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure with the nitrogen, preferably of five, six, or seven members.

The present invention is directed preferably to a method for inhibiting the premature polymerization of ethylenically unsaturated monomers comprising adding to said monomers an effective amount of a mixture comprising:

A) at least one inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the atoms necessary to form a five-, six-, or seven-membered heterocyclic ring and B) at least one inhibitor selected from the group consisting of ortho-quinone, ortho-hydroquinone, para-quinone, para-hydroquinone, and derivatives of the foregoing. The atoms necessary to complete the ring referred to above are preferably carbon atoms, but heteroatoms, such as O, N, P, or S, may also be present.

The effective amount of the combination of nitroxyl compound and quinone/hydroquinone is typically about 1 to 2,000 ppm, based on the weight of the ethylenically unsaturated monomer, although amounts outside this range may be appropriate depending upon the conditions of use. The amount of the combination of nitroxyl compound and quinone/hydroquinone is preferably about 5 to about 1,000 ppm, based on the weight of the ethylenically unsaturated monomer.

In another embodiment, the present invention is directed to a composition comprising:
(a) an ethylenically unsaturated monomer, and
(b) an effective inhibiting amount, to prevent premature polymerization of the ethylenically unsaturated monomer, of a mixture of
i) at least one inhibitor having the structural formula:

(I)

and ii) at least one inhibitor selected from the group consisting of ortho-quinone, ortho-hydroquinone, para-quinone, para-hydroquinone, and derivatives of the foregoing.

In formula (I), $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl and $X_1$ and $X_2$ (1) are independently selected from the group consisting of halogen, cyano, $COOR_7$, —S—$COR_7$, —$OCOR_7$, (wherein $R_7$ is alkyl or aryl), amido, —S—$C_6H_5$, carbonyl, alkenyl, or alkyl of 1 to 15 carbon atoms, or (2) taken together, form a ring structure with the nitrogen, preferably of five, six, or seven members.

In a preferred embodiment, the present invention is directed to a composition comprising:

(a) an ethylenically unsaturated monomer, and
(b) an effective inhibiting amount, to prevent premature polymerization of the ethylenically unsaturated monomer, of a mixture of
  (i) 1 to 99 percent by weight, based on the total weight of components (i) and (ii), of at least one inhibitor having the structural formula:

and, correspondingly,
  (ii) 99 to 1 percent by weight of at least one inhibitor selected from the group consisting of ortho-quinone, ortho-hydroquinone, para-quinone, para-hydroquinone, and derivatives of the foregoing, wherein $R_1$, $R_2$, $R_3$, $R_4$, $X_1$, and $X_2$ are as described above.

The preferred amounts of components (i) and (ii) are 10 to 90 percent by weight of component (i) and, correspondingly, 90 to 10 percent by weight of component (ii); more preferably, 20 to 80 percent by weight of component (i) and, correspondingly, 80 to 20 percent by weight of component (ii); and most preferably, 20–50 percent by weight of component (i) and 50–80 percent by weight of component (ii).

DESCRIPTION OF THE PREFERRED EMBODIMENTS

As stated above, in one preferred aspect, the present invention is directed to a method for inhibiting the premature polymerization of ethylenically unsaturated monomers comprising adding to said monomers an effective amount of a mixture comprising:

A) at least one inhibitor having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the  portion represents the atoms necessary to form a five-, six-, or seven-membered heterocyclic ring; and B) at least one inhibitor selected from the group consisting of ortho-quinone, ortho-hydroquinone, para-quinone, para-hydroquinone, and derivatives of the foregoing.

Accordingly, one of the several classes of cyclic nitroxides that can be employed in the practice of the present invention can be represented by the following structural formula:

wherein $Z_1$, $Z_2$, and $Z_3$ are independently selected from the group consisting of oxygen, sulfur, secondary amines, tertiary amines, phosphorus of various oxidation states, and substituted or unsubstituted carbon atoms, such as $>CH_2$, $>CHCH_3$, $>C=O$, $>C(CH_3)_2$, $>CHBr$, $>CHCl$, $>CHI$, $>CHF$, $>CHOH$, $>CHCN$, $>C(OH)CN$, $>CHCOOH$, $>CHCOOCH_3$, $>CHCOOC_2H_5$, $>C(OH)COOC_2H_5$, $>C(OH)COOCH_3$, $>C(OH)CHOHC_2H_5$, $>CNR_5R_6$, $>CCONR_5R_6$, $>CH=NOH$, $>C=CH-C_6H_5$, $>CF_2$, $>CCl_2$, $>CBr_2$, $>CI_2$, $>CPR_{13}R_{14}R_{15}$, and the like, where $R_5$ and $R_6$ are independently selected from the group consisting of hydrogen, alkyl, aryl, and acyl and $R_{13}$, $R_{14}$, and $R_{15}$ are independently selected from the group consisting of unshared electrons, alkyl, aryl, $=O$, $OR_{16}$, and $NR_{17}R_{18}$, where $R_{16}$, $R_{17}$, and $R_{18}$ are independently selected from the group consisting of hydrogen, alkyl, and aryl. Where $R_5$ and/or $R_6$ are alkyl, it is preferred that they be a lower alkyl (i.e., one having one to four carbon atoms, e.g., methyl, ethyl, propyl, butyl, and isomers thereof).

Where $R_5$ and/or $R_6$ are aryl, it is preferred that they be aryl of from 6 to 10 carbon atoms, e.g, phenyl or naphthyl, which, in addition, may be substituted with noninterfering substituents, e.g., lower alkyl groups, halogens, and the like.

Where $R_5$ and/or $R_6$ are acyl, it is preferred that they be acyl of the structure where $R_{19}$ is alkyl, aryl, $OR_{20}$, or $NR_{20}R_{21}$ and where $R_{20}$ and $R_{21}$ are alkyl, aryl, or where $R_{22}$ is alkyl or aryl. Where $R_{19}$, $R_{20}$, $R_{21}$, or $R_{22}$ are alkyl, they are preferably alkyl of from 1 to 15 carbon atoms, more preferably lower alkyl of from one to four carbon atoms, as described above. Where $R_{19}$, $R_{20}$, $R_{21}$, or $R_{22}$ are aryl, they are preferably aryl of from 6 to 10 carbon atoms, as described above.

Another of the several classes of cyclic nitroxides that can be employed in the practice of the present invention can be represented by the following structural formula:

wherein $Z_1$ and $Z_2$, which may be the same or different, are nitrogen or substituted or unsubstituted carbon atoms, such as =C(H)—, =C(CH$_3$)—, =C(COOH)—, =C(COOCH$_3$)—, =C(COOC$_2$H$_5$)—, =C(OH)—, =C(CN)—, =C(NR$_5$R$_6$)—, =C(CONR$_5$R$_6$)—, and the like, and where $Z_3$, $R_5$, and $R_6$ are as described above.

The cyclic nitroxides employed in the practice of the present invention can also be derived from five-membered rings. These compounds are of the structure:

wherein $Z_2$ and $Z_3$, which may be the same or different, are sulfur, oxygen, secondary amines, tertiary amines, phosphorus of various oxidation states, or substituted or unsubstituted carbon atoms, such as >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CNR$_5$R$_6$, >CCONR$_5$R$_6$, >CH=NOH, >C=CH—C$_6$H$_5$, CF$_2$, CCl$_2$, CBr$_2$, CI$_2$, >CPR$_{13}$R$_{14}$R$_{15}$, and the like, wherein the several R groups are as described above.

The cyclic nitroxides employed in the practice of the present invention can also have the structure:

wherein $Z_4$ and $Z_5$, which can be the same or different, can be nitrogen or a substituted or unsubstituted carbon atom, such as =C(H)—, =C(CH$_3$)—, =C(COOH)—, =C(COOCH$_3$)—, =C(COOC$_2$H$_5$)—, =C(OH)—, =C(CN)—, =C(NR$_5$R$_6$)—, =C(CONR$_5$R$_6$)—, and the like, where $R_5$ and $R_6$ are as described above.

Another class of cyclic nitroxides that can be employed in the practice of the present invention is of the structure:

wherein $Z_2$ and $Z_3$, which may be the same or different, are sulfur, oxygen, secondary amines, tertiary amines, or substituted or unsubstituted carbon atoms, such as >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CNR$_5$R$_6$, >CCONR$_5$R$_6$, >CH=NOH, >C=CH—C$_6$H$_5$, CF$_2$, CCl$_2$, CBr$_2$, CI$_2$, and the like, where $R_5$ and $R_6$ are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl. The alkyl (or heteroatom-substituted alkyl) groups $R_1$ through $R_4$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that $R_1$ through $R_4$ be independently selected lower alkyl (or heteroatom-substituted is lower alkyl) of one to four carbon atoms (e.g., methyl, ethyl, propyl, butyl, and isomers thereof). Where heteroatom substituents are present, they can, for example, include halogen, oxygen, sulfur, nitrogen, and the like. It is most preferred that all of $R_1$ through $R_4$ be methyl.

Examples of suitable nitroxide free radical compounds that can be used in combination with the quinone/hydroquinone inhibitor in the practice of the present invention, include, but are not limited to:
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetraethyl-1,2,5,6-tetrahydropyridine-1-oxyl;
4-carboxy-2,2,6,6-tetramethyl-1,2,5,6-tetrahydropyridine-1-oxyl;
4-carboethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;

4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3'-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)n-butylmalonate;
bis(1-oxyl-2,2,6,6-tetramethylpiperidin-4-yl)phthalate;
bis(1-oxyl-2,2,6,6-tetramethylpiperidin-4-yl)isophthalate;
bis(1-oxyl-2,2,6,6-tetramethylpiperidin-4-yl)terephthalate;
bis(1-oxyl-2,2,6,6-tetramethylpiperidin-4-yl) hexahydroterephthalate;
N,N'-bis(1-oxyl-2,2,6,6-tetramethylpiperidin-4-yl) adipamide;
N-(1-oxyl-2,2,6,6-tetramethylpiperidin-4-yl)-caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine;
4,4'-ethylenebis(1-oxyl-2,2,6,6-tetramethylpiperazin-3-one);
and the like.

It is preferred that one member of the combination employed in the practice of the present invention be 4-amino-2,2,6,6-tetramethyl-piperidinyloxy (4-amino-TEMPO), 4-oxo-2,2,6,6-tetramethylpiperidinyloxy (4-oxo-TEMPO), 4-hydroxy-2,2,6,6-tetramethylpiperidinyloxy (4-hydroxy-TEMPO), or 2,2,6,6-tetramethyl-piperidinyloxy (TEMPO).

Blends of two or more of the foregoing, e.g., 4-amino-TEMPO and 4-oxo-TEMPO, can also be employed.

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.) They are suitable for use over a wide range of temperatures, but distillation temperatures employed with the ethylenically unsaturated monomers that are stabilized by the process of the present invention typically range from about 40° C. to about 180° C., preferably from about 70° C. to about 165° C., and, more preferably, from about 80° C. to about 150° C. Such distillations are generally performed at an absolute pressure in the range of about 10 to about 1,200 mm of Hg.

As pointed out above, the quinones/hydroquinones that are used in combination with the stable nitroxide free radical compounds in the practice of the present invention can be para-quinone, para-hydroquinone, ortho-quinone, ortho-hydroquinone, or derivatives of any of the foregoing. Thus, they can be represented as having the following structural formulae:

where $R_8$, $R_9$, $R_{10}$, and $R_{11}$, are independently selected from the group consisting of hydrogen, alkyl, amino, alkoxy, aryl, cyano, halogen, hydroxyl, nitro, $SO_2Ar$, COOH, $SO_3H$, $COOR_{12}$, $NHCOR_{12}$, $OCOR_{12}$, and the like, where $R_{12}$ is alkyl, preferably of from one to five carbon atoms, and Ar is aryl. Additionally, any of $R_8$, $R_9$, $R_{10}$, and $R_{11}$, can be taken together with an adjacent R group to form one or more ring structures, preferably having five or six members and preferably aromatic. Such ring structures may also be substituted at one or more positions with groups such as alkyl, alkenyl, amino, alkoxy, aryl, cyano, halogen, hydroxyl, nitro, $SO_2Ar$, COOH, $SO_3H$, $COOR_{12}$, $NHCOR_{12}$, $OCOR_{12}$, and the like.

As examples of such quinones/hydroquinones may be listed ortho-quinone, para-quinone, β-naphthoquinone, α-naphthoquinone, anthraquinone, 2-amino-1,4-naphthoquinone, 2-methyl-1,4-naphthoquinone, 2-chloro-1,4-naphthoquinone, 2-hydroxy-1,4-naphthoquinone, 2-methoxy-1,4-naphthoquinone, 4-methoxy-1,2-naphthoquinone, 4-amino-1,2-naphthoquinone, 1,2-naphthoquinone-4-sulfonate, 4-anilino-1,2-naphthoquinone, 2-methyl-3-bromo-1,4-naphthoquinone, phthiocol, lin-naphthindazole-4,9-quinone, 1-methyl-lin-naphthotriazole-4,9-quinone, 6-bromo-1,2-naphthoquinone, 3-nitro-1,2-naphthoquinone, 2-phenyl-1,4-benzoquinone, 2,3-dimethyl-1,4-naphthoquinone, fumigatin, spinulosin, embelin, rapanone, perezone, hydroxyperezone, perezinone, polyporic acid, atromentin, muscarufin, thelephoric acid, lawsone, juglone, plumbagin, lapachol, α-lapachone, β-lapachone, 2-hydroxy-3(β,β-dimethylvinyl)-1,4-naphthoquinone, lomatiol, dehydro-β-lapachone, isolomatiol, dunnione, allodunnione, 2,5-di-t-butyl-1,4-benzoquinone, 2,6-di-t-butyl-1,4-benzoquinone, 2,3,5,6-tetramethyl-1,4-benzoquinone, corresponding hydroquinones, and the like.

Where any of $R_8$, $R_9$, $R_{10}$, and $R_{11}$ are alkyl, they are preferably alkyl of from 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that $R_8$ through $R_{11}$ be lower alkyl (or heteroatom-substituted lower alkyl) of one to five carbon atoms (e.g., methyl, ethyl, propyl, butyl, pentyl, and isomers thereof). As employed herein, the term "alkyl" is intended to include "cycloalkyl," preferably containing five or six carbon atoms, e.g., cyclohexyl or cycloheptyl. Such cycloalkyl groups may also be substituted.

Where any of $R_8$, $R_9$, $R_{10}$, and $R_{11}$ are amino, they can be primary, secondary, or tertiary amino. Any alkyl groups attached to the nitrogen atom may have from 1 to 15 carbon atoms, preferably from 1 to 5 carbon atoms, as described above for alkyl.

Where any of $R_8$, $R_9$, $R_{10}$, and $R_{11}$ are alkoxy, they are preferably alkoxy of from 1 to 15 carbon atoms, e.g., methoxy, ethoxy, propoxy, butoxy, pentoxy, hexoxy, heptoxy, octoxy, nonoxy, decoxy, undecoxy, dodecoxy, tridecoxy, tetradecoxy, pentadecoxy, and the like, and isomers thereof, e.g., t-butoxy, 2-ethylhexoxy, and the like. It is more preferred that $R_8$ through $R_{11}$ be lower alkoxy (or heteroatom-substituted lower alkoxy) of one to five carbon atoms (e.g., methoxy, ethoxy, propoxy, butoxy, pentoxy, and isomers thereof).

Where any of $R_8$, $R_9$, $R_{10}$, and $R_{11}$ are aryl, they are preferably aryl of from 6 to 12 carbon atoms, e.g. phenyl, naphthyl, anthryl, phenanthryl, and the like, which may be substituted or unsubstituted.

It is preferred that $R_8$, $R_9$, $R_{10}$, and $R_{11}$, be selected from the group consisting of hydrogen and alkyl, preferably alkyl of from one to five carbon atoms, or that they form naphthyl, anthryl, or phenanthryl groups with the quinone/hydroquinone moiety.

The ethylenically unsaturated monomer, the premature polymerization of which is an object of the present invention, can be any such monomer for which unintended polymerization during its manufacture, storage, and/or distribution is a problem. Among those monomers that will benefit from the practice of the present invention are: vinyl aromatic monomers, such as styrene, α-methylstyrene, styrene sulfonic acid, vinyltoluene, divinylbenzenes, polyvinylbenzenes, alkylated styrene, and 2-vinylpyridine; nitrile monomers, such as acrylonitrile and methacrylonitrile; acrylate or methacrylate monomers (hereinafter "(meth)acrylate monomers), such as methyl acrylate, ethyl acrylate, methyl methacrylate, and ethyl methacrylate; acrylic acid, methacrylic acid, butadiene, chloroprene, isoprene, and the like.

The ethylenically unsaturated monomers will not necessarily be stabilized indefinitely by the presence of the inhibitor blend, especially when the monomers are heated as in distillation, but they can be considered to be stabilized as long as there is a measurable increase in the time for which they can be heated before the onset of polymerization.

Those skilled in the art will understand that, if desired, additional free radical scavengers can be included in the stabilized compositions and the methods for preparing them that are the subject of the present invention. For example, air or $O_2$, as disclosed in U.S. Pat. Nos. 5,545,782 and 5,545,786, can be added, as can the aromatic nitro compounds disclosed in U.S. Pat. No. 5,254,760, the diheterosubstituted benzene compounds having at least one transferable hydrogen, e.g., a quinone derivative such as the mono-methyl-ether of hydroquinone disclosed in European Patent Application 0 765 856 A1, the iron compounds disclosed in WO98/25872, and other inhibitors, e.g., phenolics and certain inorganic salts, well-known to those skilled in the art.

The polymerization inhibitor composition can be introduced into the monomer to be protected by any conventional method. It can be added as a concentrated solution in suitable solvents just upstream from the point of desired application by any suitable means. In addition, the individual inhibiting components can be injected separately into the distillation train along with the incoming feed or through separate entry points, provided there is an efficient distribution of the inhibitors. Since the inhibitors are gradually depleted during the distillation operation, it is generally advantageous to maintain the appropriate amount of the inhibitor mixture in the distillation apparatus by adding inhibitors during the course of the distillation process. Adding inhibitors can be done either on a generally continuous basis or intermittently, in order to maintain the concentration of inhibitor mixture above the minimum required level.

The advantages and the important features of the present invention will be more apparent from the following examples.

EXAMPLES

Procedure for Dynamic Reboiler Test with Feed Shut-Off

Preparation of Feed Solution.

T-Butylcatechol (TBC) is removed from commercially available styrene by distillation under vacuum. Removal of TBC is verified by caustic titration. The desired amount of inhibitor(s) is added to this TBC-free styrene either directly or by first making a concentrated solution of the inhibitor in TBC-free styrene followed by further dilution with TBC-free styrene.

Procedure for Dynamic Reboiler Test.

A quantity of the Feed Solution containing inhibitor (blend) at the desired charge (stated as a wt/wt total inhibitor to styrene) is added to a round-bottom flask (the "Pot") and heated to the desired temperature (usually 116° C.) and brought to reflux by adjusting the pressure/vacuum. Once the Pot contents are at temperature, a continuous stream of fresh Feed Solution is begun at a rate that will add the volume of the initial Pot solution to the Pot over a period of time called the residence time (typically one hour). At the same time that the fresh Feed Solution flow is begun, the Bottoms Stream flow is also begun. The Bottoms Stream is solution in the Pot that is removed at the same rate as the fresh Feed Solution is added. The equal flows of Feed and Bottoms streams cause the quantity in the Pot to remain constant over the time of the experiment while allowing continuous replenishment of inhibitor. This procedure simulates the way inhibitors are used in a distillation train of a plant producing vinyl monomers. The experiment continues with flow in and out of the Pot for a specified period of time, typically seven hours. Samples are collected hourly from the Bottoms Stream. These samples are analyzed for polymer content via the methanol turbidity method. The amount of polymer in the samples is an indication of effectiveness of the inhibitor being tested. The lower the amount of polymer in the hourly samples, the more effective the inhibiting system should be during normal operation of a continuous manufacture or purification process.

Procedure for Feed Shut-Off.

At the end of the Reboiler Test Run (typically seven hours), a sample is collected from the Bottoms Stream. This sample corresponds to Feed Shut-Off Time 0 minutes. The flows of fresh Feed Solution and Bottoms Stream are stopped. The vacuum and temperature are monitored and adjusted to maintain boiling at the desired temperature of the experiment. Samples are periodically removed from the Pot (typically every five minutes). These samples are analyzed for polymer content via the methanol turbidity method. Data during this time is used to generate the "Feed Shut-Off Curve" for the run.

A less steep slope in the Feed Shut-Off Curve (slower rate of polymer production over time) indicates a more effective inhibiting system in the event of a loss of feed in the plant.

A longer period of time before initiation of significant polymer formation is also an indication of a more effective inhibiting system in the event of a loss of feed in the plant. A preferred system will have a long delay prior to initiation of polymer formation followed by a slow rate of polymer production once initiated.

Figure 1:
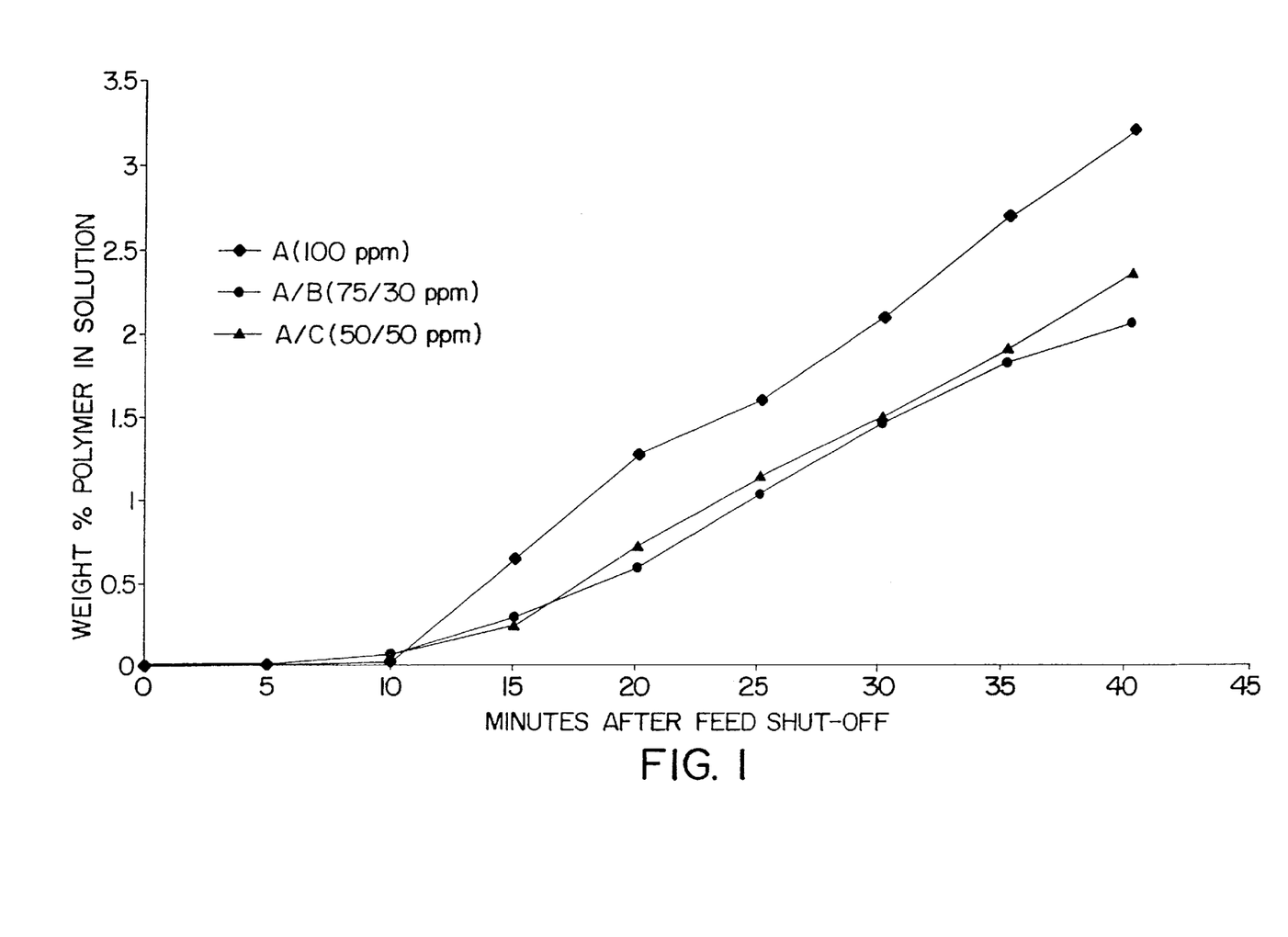
FIG. 1 is a graph showing polymer made during feed shut-off at 116° C. Prior to feed shut-off, these tests were run under dynamic conditions at 116° C. for seven hours with a one hour residence time and containing 100 or 105 ppm total inhibitor.
Figure 2:
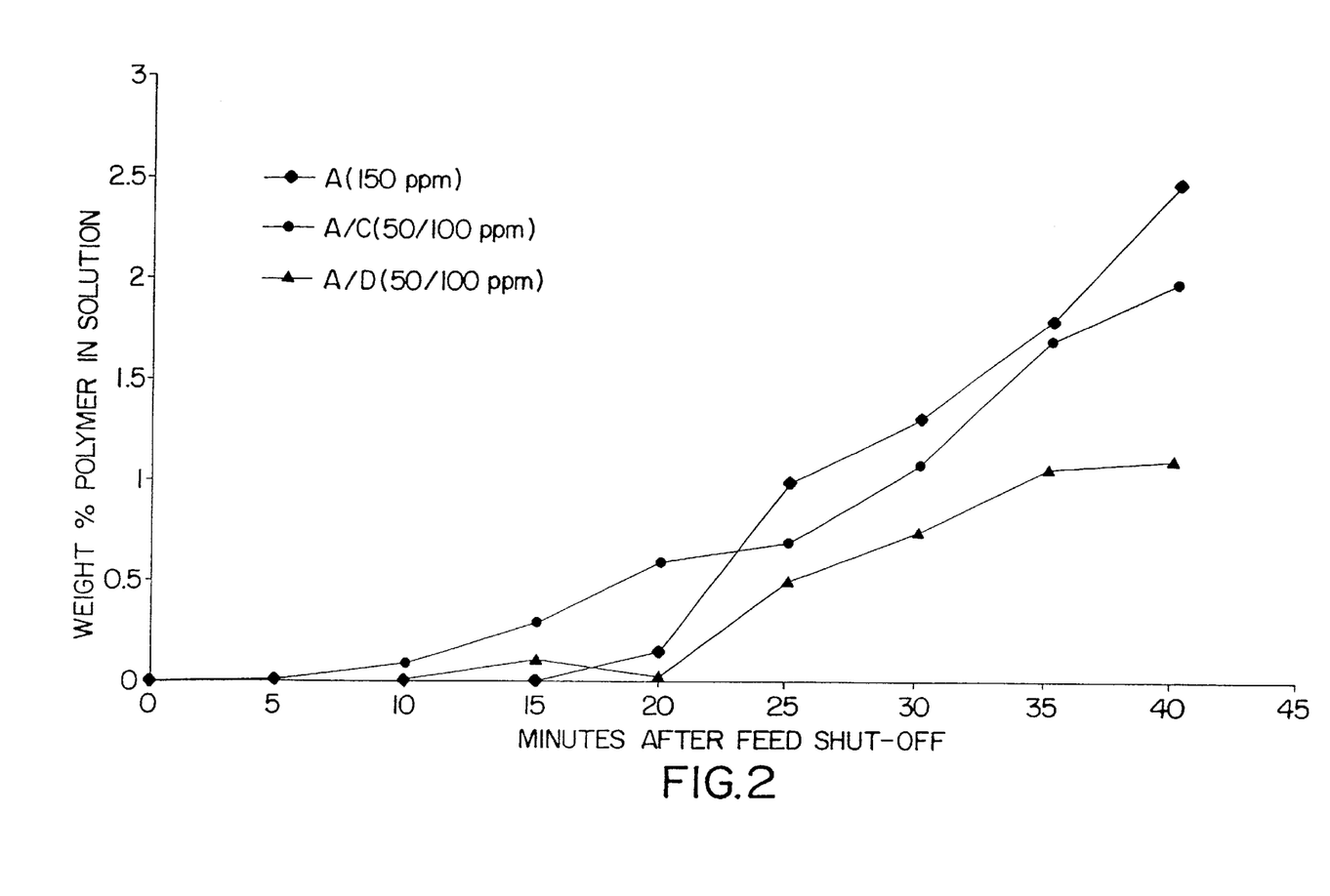
FIG. 2 is a graph showing polymer made during feed shut-off at 116° C. Prior to feed shut-off, these tests were run under dynamic conditions at 116° C. for seven hours with a one hour residence time and containing 150 ppm total inhibitor.

The above procedure is carried out using 4-oxo-TEMPO (A) alone and in combination with 2,6-di-t-butyl-1,4-benzoquinone (B), 2,5-di-t-butyl-1,4-hydroquinone (C), and 2,5-di-t-butyl-1,4-benzoquinone (D). The results are shown in FIGS. 1 and 2. The data for the graphs of FIGS. 1 and 2 are shown in Table 1.

TABLE 1

Reboiler Data for 4-oxo-TEMPO and Blends at 116° C./One-Hour Residence Time (% Polymer)

| | A (100 ppm) | A/B (75/30 ppm) | A/C (50/50 ppm) | A (150 ppm) | A/C (50/100 ppm) | A/D (50/100 ppm) | C (300 ppm) | D (300 ppm) |
|---|---|---|---|---|---|---|---|---|
| Time (hours) | | | | | | | | |
| 0 | 0 | 0 | 0 | 0 | 0 | 0 | 0 | 0 |
| 2 | 0.0058 | 0.0055 | 0.0018 | 0.0061 | 0.0053 | 0.00084 | 2.1 | 2.4 |
| 3 | 0.0087 | 0.0031 | 0.0024 | 0.006 | 0.0041 | 0.0008 | 2.1 | 3.2 |
| 4 | 0.0069 | 0.0037 | 0.0029 | 0.0051 | 0.0042 | 0.00074 | 2.4 | 3.6 |
| 5 | 0.0066 | 0.0085 | 0.006 | 0.0054 | 0.0034 | 0.00052 | 2.8 | 4.4 |
| 6 | 0.0065 | 0.012 | 0.01 | 0.0054 | 0.0031 | 0.00041 | 3.1 | 4.1 |
| 7 | 0.0077 | 0.0138 | 0.018 | 0.0052 | 0.0037 | 0.00034 | — | 3.9 |
| Time (min. after F/SO) | | | | | | | | |
| 0 | 0.007 | 0.0138 | 0.019 | 0.0057 | 0.0042 | 0.00034 | 3.1 | 3.9 |
| 5 | 0.008 | 0.0164 | 0.02 | 0.0063 | 0.0135 | — | — | — |
| 10 | 0.0212 | 0.068 | 0.066 | 0.0063 | 0.088 | 0.0118 | 3.0 | — |
| 15 | 0.64 | 0.285 | 0.244 | 0.0074 | 0.295 | 0.112 | — | — |
| 20 | 1.27 | 0.585 | 0.72 | 0.162 | 0.6 | 0.032 | 4.6 | 4.3 |
| 25 | 1.6 | 1.03 | 1.14 | 1 | 0.7 | 0.51 | — | — |
| 30 | 2.1 | 1.46 | 1.5 | 1.32 | 1.09 | 0.76 | 5.2 | 5.4 |
| 35 | 2.7 | 1.82 | 1.9 | 1.8 | 1.7 | 1.07 | — | — |
| 40 | 3.2 | 2.05 | 2.35 | 2.48 | 1.98 | 1.11 | 6.6 | 6.3 |

A is 4-oxo-TEMPO,
B is 2,6-di-t-butyl-1,4-benzoquinone,
C is 2,5-di-t-butyl-1,4-hydroquinone,
D is 2,5-di-t-butyl-1,4-benzoquinone.

As can be seen in Table 1, the combination of the present invention provides a clear and unexpected improvement over the use of any component alone, as exhibited by improved inhibition under both normal (hourly polymer) and upset (FS/O) operating conditions. All combinations of nitroxyl with hydroquinone or quinone compounds are nearly as effective or more effective than the same total amount of nitroxyl alone under normal conditions, and all combinations are better than the same total amount of nitroxyl alone under upset conditions, as shown by the amount of polymer present after 40 minutes of no feed. The comparison runs of hydroquinone or quinone alone required two to three times the total amount of inhibitor to run in a controlled fashion. At this high dosage, these compounds alone are far less effective under both normal and upset conditions than their combinations with nitroxyl. It is totally unexpected that the combination of a nitroxyl with a far less effective inhibitor, such as a hydroquinone or quinone, would provide an inhibiting system equivalent to or better than the nitroxyl itself under processing conditions.

In view of the many changes and modifications that can be made without departing from principles underlying the invention, reference should be made to the appended claims for an understanding of the scope of the protection to be afforded the invention.

What is claimed is:

1. A method for inhibiting the premature polymerization of an ethylenically unsaturated monomer selected from the group consisting of vinyl aromatic monomers, (meth)acrylate ester monomers, and nitrile monomers comprising adding to said monomer an effective amount of a mixture comprising:

A) at least one stable hindered nitroxyl compound having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, $-S-COR_7$, $-OCOR_7$, wherein $R_7$ is alkyl or aryl, amido, $-S-C_6H_5$, carbonyl, alkenyl, or alkyl of 1 to 15 carbon atoms, or (2) taken together, form a ring structure of carbon atoms with the nitrogen; and B) at least one inhibitor selected from the group consisting of ortho-quinone, ortho-hydroquinone, para-quinone, para-hydroquinone, and derivatives of the foregoing.

2. A method for inhibiting the premature polymerization of a vinyl aromatic monomer comprising adding to said monomer an effective amount of a mixture comprising:

A) at least one stable hindered nitroxyl compound having the structural formula:

wherein $R_1$ and $R_4$ are independently selected from the group consisting of hydrogen, alkyl, and hetero atom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, —S—$COR_7$, —$OCOR_7$, wherein $R_7$ is alkyl or aryl, amido, —S—$C_6H_5$, carbonyl, alkenyl, or alkyl of 1 to 15 carbon atoms, or (2) taken together, form a ring structure of carbon atoms with the nitrogen; and B) at least one inhibitor selected from the group consisting of ortho-quinone, ortho-hydroquinone, para-quinone, para-hydroquinone, and derivatives of the foregoing.

3. The method of claim 1 wherein the ethylenically unsaturated monomer is an (meth)acrylate ester monomer.

4. The method of claim 3 wherein the (meth)acrylate ester monomer is selected from the group consisting of methyl acrylate, ethyl acrylate, butyl acrylate, methyl methacrylate, and ethyl methacrylate.

5. The method of claim 1 wherein the ethylenically unsaturated monomer is a nitrile monomer.

6. The method of claim 5 wherein the the nitrile monomer is selected from the group consisting of acrylonitrile and methacrylonitrile.

7. The method of claim 1 wherein the stable hindered nitroxyl compound is of the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the portion represents the carbon atoms necessary to form a five-, six-, or seven-membered heterocyclic ring.

8. The method of claim 7 wherein the stable hindered nitroxyl compound is 4-amino-2,2,6,6-tetramethylpiperidinyloxy.

9. The method of claim 7 wherein the stable hindered nitroxyl compound is 4-oxo-2,2,6,6-tetramethylpiperidinyloxy.

10. The method of claim 7 wherein the stable hindered nitroxyl compound is 4-hydroxy-2,2,6,6-tetramethylpiperidinyloxy.

11. The method of claim 7 wherein the stable hindered nitroxyl compound is a blend of 4-amino-2,2,6,6-tetramethylpiperidinyloxy and 4-oxo-2,2,6,6-tetramethylpiperidinyloxy.

12. The method of claim 2 wherein the vinyl aromatic monomer is selected from the group consisting of styrene, α-methylstyrene, styrene sulfonic acid, vinyltoluene, divinylbenzenes, polyvinylbenzenes, alkylated styrene, and 2-vinylpyridine.

13. The method of claim 12 wherein the vinyl aromatic monomer is styrene.

14. The method of claim 13 wherein the stable hindered nitroxyl compound is 4-amino-2,2,6,6-tetramethylpiperidinyloxy.

15. The method of claim 13 wherein the stable hindered nitroxyl compound is 4-oxo-2,2,6,6-tetramethylpiperidinyloxy.

16. The method of claim 13 wherein the stable hindered nitroxyl compound is 4-hydroxy-2,2,6,6-tetramethylpiperidinyloxy.

17. The method of claim 13 wherein the stable hindered nitroxyl compound is a blend of 4-amino-2,2,6,6-tetramethylpiperidinyloxy and 4-oxo-2,26,6-tetramethylpiperidinyloxy.

18. The method of claim 7 wherein the ethylenically unsaturated monomer is styrene.

19. The method of claim 18 wherein the stable hindered nitroxyl compound is 4-amino-2,2,6,6-tetramethylpiperidinyloxy.

20. The method of claim 18 wherein the stable hindered nitroxyl compound is 4-oxo-2,2,6,6-tetramethylpiperidinyloxy.

21. The method of claim 18 wherein the stable hindered nitroxyl compound is 4-hydroxy-2,2,6,6-tetramethylpiperidinyloxy.

22. The method of claim 18 wherein the stable hindered nitroxyl compound is a blend of 4-amino-2,2,6,6-tetramethylpiperidinyloxy and 4-oxo-2,2,6,6-tetramethylpiperidinyloxy.

23. The method of claim 1 wherein the quinone/hydroquinone is:

where $R_8$, $R_9$, $R_{10}$, and $R_{11}$ are independently selected from the group consisting of hydrogen, alkyl, amino, alkoxy, aryl, cyano, halogen, hydroxyl, nitro, $SO_2Ar$, COOH, $SO_3H$, $COOR_{12}$, $NHCOR_{12}$, $OCOR_{12}$ where $R_{12}$ is alkyl, or any of $R_8$, $R_9$, $R_{10}$, and $R_{11}$ is taken together with an adjacent R group to form one or more ring structures.

24. The method of claim 23 wherein $R_8$, $R_9$, $R_{10}$, and $R_{11}$ are independently selected from the group consisting of hydrogen and alkyl or any of $R_8$, $R_9$, $R_{10}$, and $R_{11}$ is taken together with an adjacent R group to form one or more ring structures.

25. The method of claim 24 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

26. The method of claim 19 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

27. The method of claim 20 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

28. The method of claim 21 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

29. The method of claim 22 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

30. A composition comprising:

A) an ethylenically unsaturated monomer selected from the group consisting of vinyl aromatic monomers, (meth)acrylate ester monomers, and nitrile monomers, and B) an effective inhibiting amount, to prevent premature polymerization of the ethylenically unsaturated monomer, of a mixture comprising:
(a) at least one stable hindered nitroxyl compound having the structural formula:

wherein $R_1$ and $R_4$ are independently selected from the group consisting of hydrogen, alkyl, and heteroatom-substituted alkyl and $R_2$ and R3 are independently selected from the group consisting of alkyl and hetero atom-substituted alkyl; and $X_1$ and $X_2$ (1) are independently selected from the group consisting of halogen, cyano, $COOR_7$, $-S-COR_7$, $-OCOR_7$, wherein $R_7$ is alkyl or aryl, amido, $-S-C_6H_5$, carbonyl, alkenyl, or alkyl of 1 to 15 carbon atoms, or (2) taken together, form a ring structure of carbon atoms with the nitrogen; and
(b) at least one inhibitor selected from the group consisting of ortho-quinone, ortho-hydroquinone, para-quinone, para-hydroquinone, and derivatives of the foregoing.

31. A composition comprising:

A) a vinyl aromatic monomer, and

B) an effective inhibiting amount, to prevent premature polymerization of the ethylenically unsaturated monomer, of a mixture comprising:
(a) at least one stable hindered nitroxyl compound having the structural formula:

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl; and $X_1$ and $X_2$ (1) are independently selected from the group consisting of halogen, cyano, $COOR_7$, $-S-COR_7$, $-OCOR_7$, wherein $R_7$ is alkyl or aryl, amido, $-S-C_6H_5$, carbonyl, alkenyl, or alkyl of 1 to 15 carbon atoms, or (2) taken together, form a ring structure of carbon atoms with the nitrogen; and
(b) at least one inhibitor selected from the group consisting of ortho-quinone, ortho-hydroquinone, para-quinone, para-hydroquinone, and derivatives of the foregoing.

32. The composition of claim 30 wherein the ethylenically unsaturated monomer is a (meth)acrylate ester monomer.

33. The composition of claim 32 wherein the (meth)acrylate ester monomer is selected from the group consisting of methyl acrylate, ethyl acrylate, butyl acrylate, methyl methacrylate, and ethyl methacrylate.

34. The composition of claim 30 wherein the ethylenically unsaturated monomer is a nitrile monomer.

35. The composition of claim 34 wherein the the nitrile monomer is selected from the group consisting of acrylonitrile and methacrylonitrile.

36. The composition of claim 31 wherein the stable hindered nitroxyl compound is of the structural formula:

wherein $R_1$ and $R_4$ are independently selected from the group consisting of hydrogen, alkyl, and heteroatom-substituted alkyl and $R_2$, and $R_3$ are independently selected from the group consisting of alkyl and hetero atom-substituted alkyl, and the portion represents the carbon atoms necessary to form a five-, six-, or seven-membered heterocyclic ring.

37. The composition of claim 36 wherein the stable hindered nitroxyl compound is 4-amino-2,2,6,6-tetramethylpiperidinyloxy.

38. The composition of claim 36 wherein the stable hindered nitroxyl compound is 4-oxo-2,2,6,6-tetramethylpiperidinyloxy.

39. The composition of claim 36 wherein the stable hindered nitroxyl compound is 4-hydroxy-2,2,6,6-tetramethylpiperidinyloxy.

40. The composition of claim 36 wherein the stable hindered nitroxyl compound is a blend of 4-amino-2,2,6,6-tetramethylpiperidinyloxy and 4-oxo-2,2,6,6-tetramethylpiperidinyloxy.

41. The composition of claim 31 wherein the vinyl aromatic monomer is selected from the group consisting of styrene, α-methylstyrene, styrene sulfonic acid, vinyltoluene, divinylbenzenes, polyvinylbenzenes, alkylated styrene, and 2-vinylpyridine.

42. The composition of claim 41 wherein the ethylenically unsaturated monomer is styrene.

43. The composition of claim 42 wherein the stable hindered nitroxyl compound is 4-amino-2,2,6,6-tetramethylpiperidinyloxy.

44. The composition of claim 42 wherein the stable hindered nitroxyl compound is 4-oxo-2,2,6,6-tetramethylpiperidinyloxy.

45. The composition of claim 42 wherein the stable hindered nitroxyl compound is 4-hydroxy-2,2,6,6-tetramethylpiperidinyloxy.

46. The composition of claim 42 wherein the stable hindered nitroxyl compound is a blend of 4-amino-2,2,6,6-tetramethylpiperidinyloxy and 4-oxo-2,2,6,6-tetramethylpiperidinyloxy.

47. The composition of claim 36 wherein the ethylenically unsaturated monomer is styrene.

48. The composition of claim 47 wherein the stable hindered nitroxyl compound is 4-amino-2,2,6,6-tetramethylpiperidinyloxy.

49. The composition of claim 47 wherein the stable hindered nitroxyl compound is 4-oxo-2,2,6,6-tetramethylpiperidinyloxy.

50. The composition of claim 47 wherein the stable hindered nitroxyl compound is 4-hydroxy-2,2,6,6-tetramethylpiperidinyloxy.

51. The composition of claim 47 wherein the stable hindered nitroxyl compound is a blend of 4-amino-2,2,6,6-tetramethylpiperidinyloxy and 4-oxo-2,2,6,6-tetramethylpiperidinyloxy.

52. The composition of claim 30 wherein the quinone/hydroquinone is:

-continued or where $R_8$, $R_9$, $R_{10}$, and $R_{11}$ are independently selected from the group consisting of hydrogen, alkyl, amino, alkoxy, aryl, cyano, halogen, hydroxyl, nitro, $SO_2Ar$, COOH, $SO_3H$, $COOR_{12}$, $NHCOR_{12}$, $OCOR_{12}$ where $R_{12}$ is alkyl, or any of $R_8$, $R_9$, $R_{10}$, and $R_{11}$ is taken together with an adjacent R group to form one or more ring structures.

53. The composition of claim 52 wherein $R_8$, $R_9$, $R_{10}$, and $R_{11}$ are independently selected from the group consisting of hydrogen and alkyl or any of $R_8$, $R_9$, $R_{10}$, and $R_{11}$ is taken together with an adjacent R group to form one or more ring structures.

54. The composition of claim 53 wherein the wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

55. The composition of claim 48 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

56. The composition of claim 49 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

57. The composition of claim 50 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

58. The composition of claim 51 wherein the quinone/hydroquinone is selected from the group consisting of 2,6-di-t-butyl-1,4-benzoquinone, 2,5-di-t-butyl-1,4-benzoquinone, 2,5-di-t-butyl-1,4-hydroquinone, and mixtures thereof.

* * * * *